US008307693B2

(12) United States Patent
Uram et al.

(10) Patent No.: US 8,307,693 B2
(45) Date of Patent: Nov. 13, 2012

(54) DEVICES, SYSTEMS AND METHOD FOR CALIBRATION OF SYSTEMS

(75) Inventors: Martin J. Uram, Pittsburgh, PA (US); Michael G. Frazier, Lower Burrell, PA (US); Kenton E. Adams, Allison Park, PA (US)

(73) Assignee: Medrad, Inc., Indianola, PA (US)

( * ) Notice: Subject to any disclaimer, the term of this patent is extended or adjusted under 35 U.S.C. 154(b) by 512 days.

(21) Appl. No.: 11/736,802

(22) Filed: Apr. 18, 2007

(65) Prior Publication Data
US 2007/0244428 A1 Oct. 18, 2007

Related U.S. Application Data

(62) Division of application No. 11/391,151, filed on Mar. 28, 2006, now abandoned.

(60) Provisional application No. 60/665,687, filed on Mar. 28, 2005.

(51) Int. Cl.
*G01F 19/00* (2006.01)
(52) U.S. Cl. ........................................ 73/1.74
(58) Field of Classification Search .................. 73/1.36, 73/1.74
See application file for complete search history.

(56) References Cited

U.S. PATENT DOCUMENTS

| | | | |
|---|---|---|---|
| 4,331,262 A | | 5/1982 | Snyder et al. |
| 4,342,218 A | | 8/1982 | Fox |
| 4,384,470 A | * | 5/1983 | Fiore ............................. 73/1.68 |
| 4,610,256 A | * | 9/1986 | Wallace ........................ 600/488 |
| 4,815,313 A | * | 3/1989 | Beard ............................ 73/1.62 |
| 5,140,862 A | | 8/1992 | Pappalardo |

(Continued)

FOREIGN PATENT DOCUMENTS
WO 9308454 * 4/1993

*Primary Examiner* — Robert R Raevis
(74) *Attorney, Agent, or Firm* — Jill Denesvich

(57) ABSTRACT

An injector system for use in injecting a fluid into a patient includes a communication system adapted to receive data from at least a first sensor that measures a value first variable. The communication system is also adapted to receive data from a calibrated sensor that measures a value the first variable. The injector system further includes a calibration system adapted to calibrate output from the first sensor in response to output from the calibrated sensor. An injector for use in injecting a fluid into a patient, includes a first sensor that measures a value first variable, a communication port adapted to receive data from a calibrated sensor that measures the value the first variable, and a controller adapted to compare data from the calibrated sensor with data from the first sensor and to calibrate output from the first sensor. The devices, systems and methods of the present invention are applicable to systems other than injection systems. For example, a method for calibrating a system (for example, an injector system) includes: placing a calibrated sensor in communication with the system; making a measurement of the value of at least a first variable with the calibrated sensor; transmitting the measured value from the calibrated sensor to the system via a data communication system in operative connection between the calibrated sensor and the system; making a measurement of the value of the first variable with a sensor of the system at approximately the same time as the measurement made with the calibrated sensor; comparing the value of the first variable measured with the calibrated sensor with the value of the first variable measured with the system sensor; and calibrating the output of the system sensor at least in part based upon the comparison.

9 Claims, 1 Drawing Sheet

U.S. PATENT DOCUMENTS

| | | | |
|---|---|---|---|
| 5,174,038 A * | 12/1992 | Neyens et al. | 33/521 |
| 5,263,367 A | 11/1993 | Pippert | |
| 5,630,935 A | 5/1997 | Treu | |
| 5,684,246 A | 11/1997 | Korpi | |
| 5,808,203 A | 9/1998 | Nolan, Jr. et al. | |
| 6,422,057 B1 | 7/2002 | Anderson | |
| 7,291,131 B2 * | 11/2007 | Call | 604/187 |
| 2002/0016569 A1 | 2/2002 | Critchlow et al. | |
| 2003/0171712 A1 | 9/2003 | Critchlow et al. | |
| 2008/0045919 A1 * | 2/2008 | Jakob et al. | 604/406 |

\* cited by examiner

DEVICES, SYSTEMS AND METHOD FOR CALIBRATION OF SYSTEMS

CROSS-REFERENCE TO RELATED APPLICATIONS

This application for patent claims the benefit of U.S. application Ser. No. 11/391,151, filed 28 Mar. 2006, now abandoned which claims priority to U.S. Provisional Application Ser. No. 60/665,687, filed 28 Mar. 2005. These applications have been assigned to the assignee of the invention disclosed below, and their teachings are incorporated into this document by reference.

BACKGROUND OF THE INVENTION

The present invention relates generally to devices, systems and methods for calibration of systems such as injectors and, particularly, to devices, system and methods for pressure calibration of injectors used to inject fluid into a patient (either a human or a so-called lower animal).

In many medical diagnostic and therapeutic procedures, a physician or other person injects a patient with a fluid. Over the past several decades, a number of injector-actuated syringes and powered injectors for pressurized injection of fluids such as contrast media have been developed for use in procedures such as angiography, computed tomography, ultrasound and NMR/MRI. In many applications, these powered injectors are designed to deliver a preset amount of contrast media at a preset flow rate.

To ensure the safety of the patient, the operation of a powered injector should be carefully controlled. For example, it is desirable to not exceed a certain fluid pressure during an injection procedure. In addition to potential hazards to the patient (for example, vessel damage) and potential degradation of the diagnostic and/or therapeutic utility of the injection fluid, excessive pressure can lead to equipment failure. For example, because of the potential of cross-contamination between patients, the syringe and tubing used to carry fluid to a patient are typically changed on a per-patient basis. Such disposable syringes and other fluid path components (sometimes referred to collectively as a "disposable set") are typically fabricated from plastics of various burst strengths. If the injector causes pressure in the fluid path to rise above the burst strength of a disposable fluid path element, the fluid path element will fail.

Direct measurement of fluid pressure in a syringe is often difficult. In controlling system or injection pressure, many currently available injectors thus use an indirect indication of syringe/system pressure. For example, motor current can be measured and related to fluid pressure through an algorithm. Likewise, force upon a component of the injector system can be measured (using, for example, a strain gauge) and similarly related to fluid pressure. Pressure measurement and control of fluid pressure are discussed, for example, in U.S. Pat. No. 5,808,203 and in Published U.S. Patent Application Nos. 2003/0171712 and 2002/0016569, assigned to the assignee of the present invention, the disclosures of which are incorporated herein by reference.

Whatever pressure measurement technique or mechanism is used to provide an estimate of fluid pressure, periodic calibration of the measurement system is required to ensure the accuracy of the measurement. Typically, an initial calibration is made at the time of manufacture and periodic calibrations are carried out thereafter. Under current practice, a technician trained in injector calibration must perform the periodic calibrations. In general a needle valve assembly is connected to the injector to simulate a "perfect syringe". A pressure transducer is placed in fluid connection with the needle valve assembly. The technician runs the system through a testing procedure in which various known pressures are generated sequentially (for example, four individual pressures (for example, 0, 100 psi, 150 psi and 300 psi) are generated in one calibration procedure). A syringe can, for example, be filled and fluid injected into a waste container during the injection procedure. The pressure determined by the injector pressure measuring mechanism(s) is calibrated to the actual measure pressure as determined by the pressure transducer. The pressure calibration procedure can, for example, take ½ hour to an hour if no problems arise. During this time, the injector is unavailable to the medical staff. Moreover, errors or inaccuracies can be introduced by the calibrating technician. For example, among other tasks, the calibrating technician must accurately read the output of the pressure transducer at the correct time and accurately adjust the needle valve system to achieve a desired pressure.

It is desirable to develop improved calibration devices, systems and methods that reduce or eliminate the above and/or other problems with currently available sensor calibration devices, systems and methods.

SUMMARY OF THE INVENTION

In one aspect, the present invention provides an injector system for use in injecting a fluid into a patient. The injector system includes a communication system adapted to receive data from at least a first sensor that measures a value first variable. The communication system is also adapted to receive data from a calibrated sensor that measures a value the first variable. The injector system further includes a calibration system adapted to calibrate output from the first sensor in response to output from the calibrated sensor. The first variable can, for example, be fluid pressure, temperature, fluid flow rate, fluid viscosity or position of a pressuring member of the injector system (for example, the position of a drive member adapted to cooperate with a syringe plunger).

The injector system can also include an adapter in operative connection between the calibrated sensor and the communication system to convert output from the calibrated sensor to a form suitable for communication to the communication system. The injector system can further include a control system adapted to change the value of the variable so that multiple values can be measured by the first sensor and the calibrated sensor.

In one embodiment, the variable measured by first sensor and the calibrated sensor is fluid pressure. The injector system can, for example, change the fluid pressure over a period of time and multiple, synchronized data readings of the output from the calibrated sensor and from the first sensor can be made. In one embodiment, a comparison of the data from the calibrated sensor to the data from the first sensor is made and the output from the first sensor is calibrated at least in part on the bases of the comparison. The injector system can further include a processor in communicative connection with a memory. The memory can have stored therein a computer program to perform the comparison and to calibrate the data from the first sensor. The computer program can also initiate the change in fluid pressure over a period of time.

In another aspect, the present invention provides an injector for use in injecting a fluid into a patient, including: a first sensor that measures a value first variable, a communication port adapted to receive data from a calibrated sensor that measures the value the first variable, and a controller or a controller system adapted to compare data from the calibrated sensor with data from the first sensor and to calibrate output from the first sensor. In one embodiment, the controller or controller system is also adapted to effect a change in the variable over a period of time so that readings of data from the first variable and data from the calibrated sensor can be made over a range of values of the first variable. In one embodiment, the variable is fluid pressure.

In another aspect, the present invention provides a method for calibrating an injector for use in injecting a fluid into a patient; including: placing a calibrated sensor in communication with the injector; making a measurement of the value of at least a first variable with the calibrated sensor; transmitting the measured value from the calibrated sensor to the injector via a data communication system in operative connection between the calibrated sensor and the injector; making a measurement of the value of the first variable with a sensor of the injector at approximately the same time as the measurement made with the calibrated sensor; comparing the value of the first variable measured with the calibrated sensor with the value of the first variable measured with the injector sensor; and calibrating the output of the injector sensor at least in part based upon the comparison.

The method can further include the steps: changing the value of the variable over a period of time; making a measurement of the value of at least a first variable with the calibrated sensor at multiple values of the first variable; and making a measurement of the value of the first variable with a sensor of the injector at approximately the same time as the measurement made with the calibrated sensor at multiple values of the variable. As described above, the injector can be controlled to change the value of the variable (preferably, in an automated fashion or without user intervention).

The devices, systems and methods of the present invention are applicable to systems other than injection systems. In still another aspect, the present invention thus provides a method for calibrating a system including: placing a calibrated sensor in communication with the system; making a measurement of the value of at least a first variable with the calibrated sensor; transmitting the measured value from the calibrated sensor to the system via a data communication system in operative connection between the calibrated sensor and the system; making a measurement of the value of the first variable with a sensor of the system at approximately the same time as the measurement made with the calibrated sensor; comparing the value of the first variable measured with the calibrated sensor with the value of the first variable measured with the system sensor; and calibrating the output of the system sensor at least in part based upon the comparison.

Likewise, in a further aspect, the present invention provides a system including a communication system adapted to receive data from at least a first sensor that measures a value first variable. The communication system is also adapted to receive data from a calibrated sensor that measures a value the first variable. The system further includes a calibration system adapted to calibrate output from the first sensor in response to output from the calibrated sensor. The first variable can, for example, be fluid pressure, temperature, fluid flow rate, fluid viscosity, position or virtually any other variable.

The system can also include an adapter in operative connection between the calibrated sensor and the communication system to convert output from the calibrated sensor to a form suitable for communication to the communication system. The system can further include a control system adapted to change the value of the variable so that multiple values can be measured by the first sensor and the calibrated sensor.

In still a further aspect, the present invention provides a system, including: a first sensor that measures a value first variable, a communication port adapted to receive data from a calibrated sensor that measures the value the first variable, and a controller or a controller system adapted to compare data from the calibrated sensor with data from the first sensor and to calibrate output from the first sensor. In one embodiment, the controller or controller system is also adapted to effect a change in the variable over a period of time so that readings of data from the first variable and data from the calibrated sensor can be made over a range of values of the first variable.

The calibration devices, systems and method of the present invention provide a number of advantages over current techniques. For example, in an injection system, the time to conduct a pressure calibration can be reduced from, for example, approximately ½ hour to a matter of seconds (for example, approximately 15 seconds), resulting in a significant reduction of downtime of injection equipment and medical staff. Moreover, the calibration devices, systems and methods of the present invention result in periodic "in the field" pressure calibrations that are generally as accurate as the "production" calibration occurring at the time of manufacture. In that regard, automation of the calibration process (via the injector and associated software) eliminates manual intervention, resulting in stable and repeatable calibrations. The calibration devices, systems and methods of the present invention are also less complex for production and field personnel. In general, existing injectors are readily retrofitted to practice the calibration methods of the present invention.

BRIEF DESCRIPTION OF THE DRAWINGS

Other aspects of the invention and their advantages will be discerned from the following detailed description when read in connection with the accompanying drawings, in which.

DETAILED DESCRIPTION OF THE INVENTION

Several representative embodiments of the present invention are discussed in connection with the retrofitting of a STELLANT® Injector available from Medrad, Inc. of Indianola, Pa. for use with the calibration devices, systems and method of the present invention to calibrate one or more pressure measuring systems of the injector. However, one skilled in the art appreciates that the calibration devices, systems and methods are suitable for use in generally any injector system or in any other system to calibrate generally any measured variable.

Figure 1:
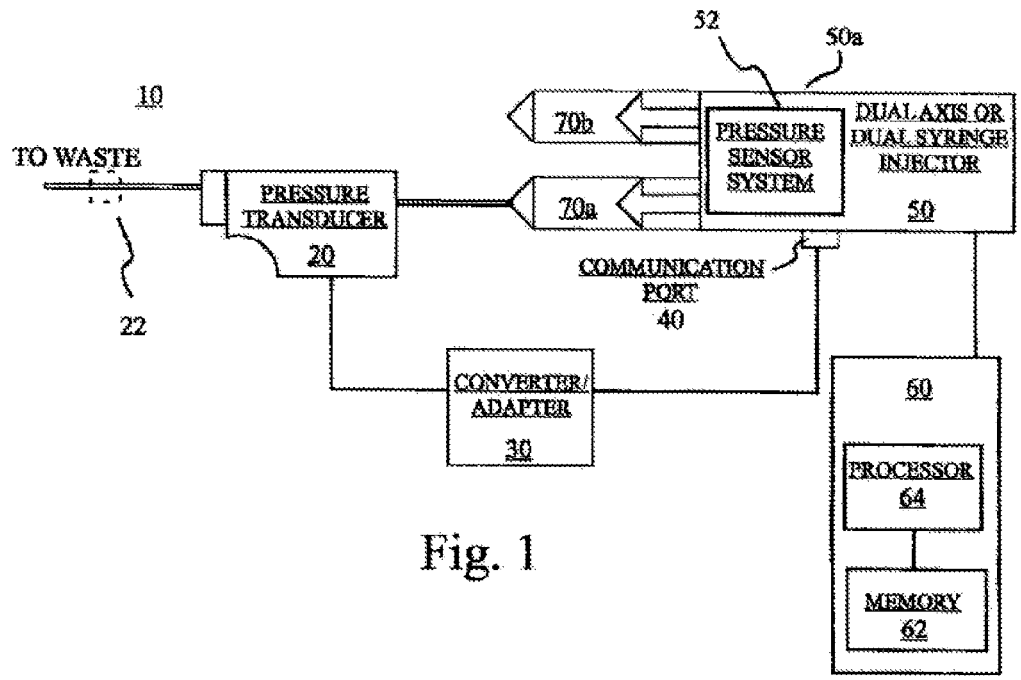
FIG. 1 illustrates schematically one embodiment of a pressure calibration system of the present invention.

In general, the pressure calibration devices, systems and methods of the present invention enable pressure calibration of an injector to be automatically performed by the injector with no (or minimal) user/manual interaction. In several embodiments of pressure calibration, this result is accomplished by communicating to the injector the output of a pressure transducer mounted on or placed in fluid connection with the tip of a syringe at the same time that the injector periodically samples the "indirect" pressure measurement monitoring system of the injector (for example, a strain gauge signal and/or a motor current signal). In one embodiment, the sampling occurs during a "calibration injection" protocol or procedure in which a pressure is incrementally changed (for example, increases or ramped). The calibration injection protocol or procedure can, for example, be stored in a memory in the injector and be carried out in an automated fashion upon initiation of calibration. The synchronized reading of the signal(s) from the indirect measurement(s) of fluid pressure and the actual (calibrated), directly measured fluid pressure allows the injector's indirect measurement system to be calibrated to the actual pressure (as measured by, for example, a calibrated pressure transducer). An embodiment of such a calibration system 10 is illustrated in FIG. 1 for a dual-syringe or dual-axis injector 50. The devices, systems and methods of the present invention are, however, equally applicable to a single-syringe or single-axis injector.

In several studies of the present invention a Model MC-1753 MultiCal Pressure Module pressure transducer 20 was connected to an external buffer module or signal adapter 30 to convert the output signal from the pressure transducer to a signal suitable for communication to injector 50. In these studies, adapter 30 was placed in communicative connection with a communication port 40 on a STELLANT® injector 50 available from Medrad, Inc. of Indianola, Pa. In that regard, a commercially available STELLANT injector was retrofitted for communication with adapter 40 through a handswitch communication port or connector 40 located on the case of the injector head.

The pressure transducer used in the study was suitable to measure hydraulic pressure up to 2,000 psi and output the pressure signal as a 0 to 2 V signal on two 4-mm banana jacks. These two signals were connected to signal adapter 30. Signal adapter or interface module 30 provides signal buffering and was able to convert the banana jack signals to, for example, a Micro D-Sub plug configuration to mate to the connectors/jacks of handswitch communication port 40 mounted on the injector case. Internal to injector 50, two unused wires on handswitch communication port 40 were routed to an unused analog input channel on a controller/microprocessor board within injector 50.

In several studies, pressure calibrations were performed by attaching a syringe (preferably a calibrated syringe as known in the art) to the injector. In one set of studies, a closed stopcock 22 (see FIG. 1) was attached to syringe 70a. An injection at a constant flowrate was performed into the closed stopcock until a maximum pressure was reached. In another set of studies, the outflow from syringe 70a was directed to a waste container.

During the injection, calibration software (for example, PC based software or software internal to or part of the injector 50—as, for example, stored in a memory 62 in communicative connection with one or more processors 64 of a controller 60 of injector 50) samples signals from a pressure monitoring system 52 (including, for example, a strain gauge signal and a motor current monitoring system signal) as well as a signal from pressure transducer 20 periodically to accumulate a series of readings. In several studies performed to illustrate the viability of the present invention, calibration software stored on a PC was used. After sampling, the calibration software performed an algorithmic fit (for example, a least squares fit) to the data. In the case of a least squares fit, the calibration software determined the gain and offset for a linear calibration equation. The calibration constants determined by the fit were then stored in the injector's long-term memory using currently available methods. Alternatively, signal readings can be sampled and stored by embedded code in the injector and then transferred to external calibration software, where, for example, a least squares fit can be done. Moreover, as described above, all calibration software can be stored in memory 62 of the injector and executed by processor 64 of injector 50.

Figure 2:
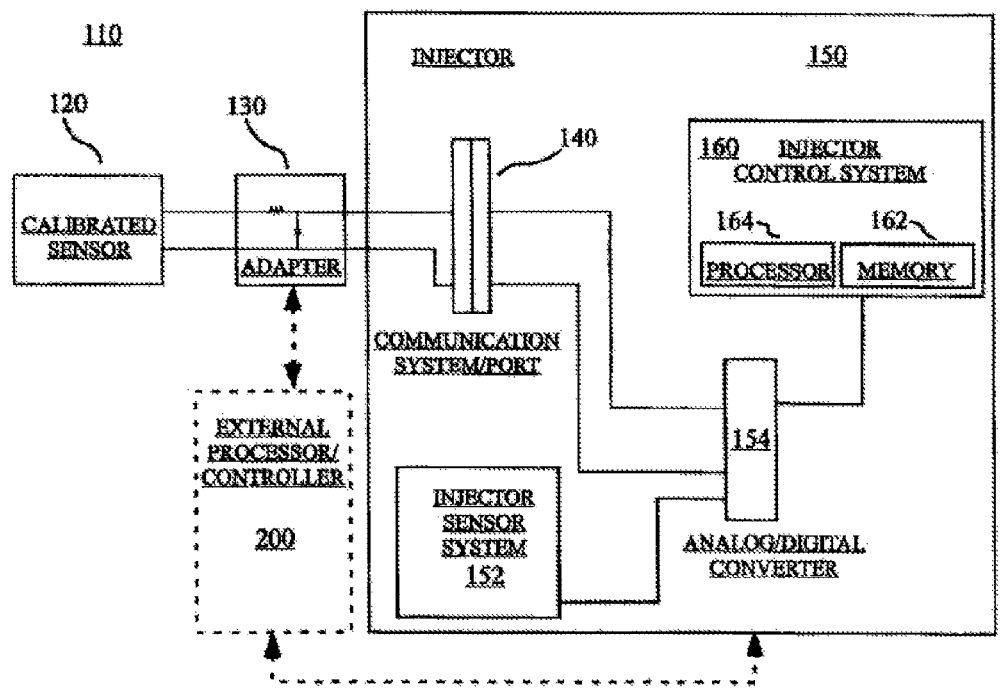
FIG. 2 illustrates schematically another embodiment of a calibration system of the present invention.

FIG. 2 illustrates schematically a general embodiment of a injector/calibration system 110 of the present invention. In general, the calibration devices, systems and methods of the present invention can be used to calibrate virtually any type of sensor or sensor system 152 (which may include more than one sensor or sensing mechanism) used in an injector 150 to measure virtually any variable (for example, pressure, flow rate, plunger position, temperature, viscosity etc.) Injector system 110 includes a calibrated sensor 120 that is used to provide a calibrated measurement of a variable. As illustrated in FIG. 2, the signal from calibrated sensor 120 can be transmitted (for example, without operator/manual interaction or intervention) to an adapter or converter 130. A converted signal is transmitted (for example, without operator/manual interaction or intervention) from adapter 130 to a communication port 140 of the injector communication system. In an alternative embodiment, sensor 120 can communicate directly with the injector communication system, should no conversion of the signal from sensor 120 be required. In the embodiment of FIG. 2, a signal from communication port 140 is communicated to an analog/digital converter 154 to provide a digital signal to injector controller 160. An analog/digital converter 154 is not needed in the case that the output (for example, digital output) from calibrated sensor 120 is suitable for direct communication with injector control system 160. As clear to one skilled in the art, many alternative communication paths, protocols and/or connections are suitable for the components of the present invention. Moreover, communication can be through wired connection or wireless, using a variety of known communication protocols (for example, Ethernet, Bluetooth etc.).

Injector control system 160 includes software in memory 162 in communication with processor 164 through which synchronized measurements of the value of the measured variable of interest from the calibrated sensor 120 and from the injector sensor system 152 are made. In that regard, the variable of interest is preferably changed over time (for example, by control system 160 of 150 injector via software stored in memory 162) and synchronized measurements from calibrated sensor 120 and injector sensor system 152 are collected over a number of points. The measurements from calibrated sensor 120 are used to calibrate the output of sensor system 152. For example, as described above, a least squares fit of the data can be made wherein the calibration software determines the gain and offset for a linear calibration equation. As clear to one skilled in the art, many types of algorithmic functions can be used to fit the collected data.

Calibration systems 110 substantially quickens and simplifies periodic ("in the field") pressure calibrations. Indeed, in several studies of the present invention during pressure calibration, 140 individual measurements (from each of calibrated sensor 120 and injector sensor system 152) were taken over pressures ranging from 0 psi to 300 psi and injector system 110 pressure calibrated in approximately 15 seconds. In general, the calibration was as accurate as the "production" calibration which occurred at the time of manufacture. Eliminating most if not all manual intervention in the calibration process results in stable and repeatable calibrations. In that regard, unlike current calibration techniques, the output of calibrated sensor 120 is communicated directly to injector 150 without manual intervention. Moreover, injector control system 160 operates to change the measured variable (for example, fluid pressure) without manual intervention.

Injector control system 160 (components of which can be internal and/or external to the injector housing—see injector housing 50a in FIG. 1) can operate to collect the data from calibrated sensor and from injector sensing system 152 and to calibrate/correct the output from injector sensor system 152.

Likewise, control system 160 can operate to effect a controlled change of the measure variable. Alternatively, an external processor/controller 200 (for example, a PC-based processing unit) can be placed in communicative connection with injector 150 and/or with calibrated sensor 120 to perform any portion of the calibration process. The function of adapter 130 and external/processor controller 200 can be combined in a single unit. Indeed, the calibrated sensor function can also be combined in such a single unit.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. An injector system for use in injecting a fluid into a patient, comprising:
    at least one syringe having a fluid outlet;
    a drive system coupled to the syringe;
    a calibrated sensor disposed in fluid connection with the fluid outlet;
    a communication system adapted to receive data from at least an uncalibrated sensor that measures a pressure variable,
    wherein the communication system is adapted to receive data from the calibrated sensor that measures a value of the pressure variable; and
    a calibration system adapted to calibrate output from the uncalibrated sensor in response to output from the calibrated sensor,
    wherein the uncalibrated sensor is coupled to the drive system.

2. The injector system of claim 1 further comprising an adapter in operative connection between the calibrated sensor and the communication system to convert output from the calibrated sensor to a form suitable for communication to the communication system.

3. The injector system of claim 1 further comprising a control system adapted to change the value of the variable so that multiple values can be measured by the uncalibrated sensor and the calibrated sensor.

4. An injector for use in injecting a fluid into a patient, comprising:
    at least one syringe having a fluid outlet;
    a drive system coupled to the syringe;
    a calibrated sensor disposed in fluid connection with the fluid outlet;
    a pressure sensor coupled to the drive system and disposed to measure a value of a pressure variable;
    a communication system adapted to received data related to fluid pressure from the calibrated sensor; and
    a controller adapted to compare data from the calibrated sensor with data from the pressure sensor and to calibrate output from the pressure sensor.

5. The injector of claim 4 wherein the controller is also adapted to effect a change in the variable over a period of time so that readings of data from the pressure sensor and data from the calibrated sensor can be made over a range of values of the pressure variable.

6. The injector of claim 4 further comprising an adapter in operative connection between the calibrated sensor and the communication system to convert output from the calibrated sensor to a form suitable for communication to the communication system.

7. The injector of claim 4 wherein in the controller includes a processor in communicative connection with a memory, the memory having stored therein a computer program to perform the comparison and to calibrate the data from the calibrated sensor.

8. A method for calibrating a system; comprising:
    placing a calibrated sensor disposed in fluid connection with a fluid outlet of a syringe and in communication with the system;
    coupling an uncalibrated sensor to the drive system;
    making a measurement of the value of at least a pressure variable with the calibrated sensor;
    transmitting the measured value from the calibrated sensor to the system via a data communication system in operative connection between the calibrated sensor and the system;
    making a measurement of a value of the pressure variable with the uncalibrated sensor at approximately the same time as the measurement made with the calibrated sensor;
    comparing the value of the pressure variable measured with the calibrated sensor with the value of the pressure variable measured with the uncalibrated sensor; and
    calibrating the output of the uncalibrated sensor at least in part based upon the comparison.

9. The injector system for use in injecting a fluid into a patient of claim 1 wherein the uncalibrated sensor is at least one of a strain gauge or motor current system.

* * * * *

UNITED STATES PATENT AND TRADEMARK OFFICE
CERTIFICATE OF CORRECTION

PATENT NO. : 8,307,693 B2
APPLICATION NO. : 11/736802
DATED : November 13, 2012
INVENTOR(S) : Uram et al.

It is certified that error appears in the above-identified patent and that said Letters Patent is hereby corrected as shown below:

On the Title Page, in Item (57), under "ABSTRACT, in Column 2, Line 3, delete "value first" and insert -- value of the first --, therefor.

On the Title Page, in Item (57), under "ABSTRACT", in Column 2, Line 5, delete "value the first" and insert -- value of the first --, therefor.

On the Title Page, in Item (57), under "ABSTRACT", in Column 2, Line 10, delete "value first" and insert -- value of the first --, therefor.

On the Title Page, in Item (57), under "ABSTRACT", in Column 2, Line 12, delete "value the first" and insert -- value of the first --, therefor.

IN THE SPECIFICATION:

In Column 2, Line 30, delete "value first" and insert -- value of the first --, therefor.

In Column 2, Lines 32-33, delete "value first" and insert -- value of the first --, therefor.

In Column 2, Line 64, delete "value first" and insert -- value of the first --, therefor.

In Column 2, Line 66, delete "value first" and insert -- value of the first --, therefor.

In Column 3, Lines 52-53, delete "value first" and insert -- value of the first --, therefor.

In Column 3, Lines 54-55, delete "value the first" and insert -- value of the first --, therefor.

In Column 4, Line 2, delete "value first" and insert -- value of the first --, therefor.

In Column 4, Line 4, delete "value the first" and insert -- value of the first --, therefor.

In Column 5, Line 22, delete "adapter 40" and insert -- adapter 30 --, therefor.

In Column 6, Line 37, delete "150 injector" and insert -- injector 150 --, therefor.

Signed and Sealed this
Twenty-seventh Day of August, 2013

Teresa Stanek Rea
*Acting Director of the United States Patent and Trademark Office*

CERTIFICATE OF CORRECTION (continued)
U.S. Pat. No. 8,307,693 B2

IN THE CLAIMS:

Is Column 8, Line 8, in Claim 4, delete "received" and insert -- receive --, therefor.

In Column 8, Line 23, in Claim 7, delete "wherein in" and insert -- wherein --, therefor.

In Column 8, Line 28, in Claim 8, delete "system;" and insert -- system, --, therefor.

In Column 8, Line 32, in Claim 8, delete "to the" and insert -- to a --, therefor.

In Column 8, Line 33, in Claim 8, delete "of the" and insert -- of a --, therefor.

In Column 8, Line 45, in Claim 8, delete "the output" and insert -- an output --, therefor.

In Column 8, Line 49, in Claim 9, delete "or motor" and insert -- or a motor --, therefor.